(12) United States Patent
Wilson

(10) Patent No.: US 7,062,391 B2
(45) Date of Patent: Jun. 13, 2006

(54) MOTION COMPENSATION IN BIOMAGNETIC MEASUREMENT

(75) Inventor: Harold Wilson, Port Moody (CA)

(73) Assignee: VSM Medtech Systems Inc., Coquitlam (CA)

( * ) Notice: Subject to any disclaimer, the term of this patent is extended or adjusted under 35 U.S.C. 154(b) by 133 days.

(21) Appl. No.: 10/798,253

(22) Filed: Mar. 12, 2004

(65) Prior Publication Data
US 2005/0200854 A1    Sep. 15, 2005

(51) Int. Cl.
*G06F 19/00* (2006.01)
(52) U.S. Cl. .................... 702/64; 600/410; 73/649; 324/244
(58) Field of Classification Search .............. 702/65, 702/38, 37, 150, 151, 64, 182–185, 189, 702/36; 73/609, 620, 627, 645, 649, 657; 324/244–247, 244.1, 260; 600/409–411, 600/415, 424, 425, 427, 451
See application file for complete search history.

(56) References Cited

U.S. PATENT DOCUMENTS

2001/0048306 A1 * 12/2001 Mueller et al. ............. 324/334

OTHER PUBLICATIONS

Thomas Funkhouser and Michael Kazhdan, "Alignment and Matching", Aug. 1, 2000, Princeton University, pp. 9-17.*

M. Danos and L.C. Maximon; *Multiple matrix Elements of the Translation Operator*; J. Math. Phys. V.6 (1965) pp. 766-778.

A.A. Ioannides, J. Mutter, and E.-A. Barna-Popescu,; *Irreducible tensor representation of MEG signals: Theory and applications*; Proc. 12th Int. Conf. Biomagnetism, pp. 883-886, Aug. 2000.

K. Jerbi, J.C. Mosher, S. Bailet and R.M. Leahy; *On MEG forward modelling using multipolar expansions*, Phys. Med. Biol. v.47 (2002) pp. 523-555.

S. Taulu, M. Kajola and J. Simola; *The Signal Space Separation Method*; Proc. 14th Conf. of ISBET (Int. Soc. for Brain Electromagentic Topography) Nov. 2003.

* cited by examiner

*Primary Examiner*—Edward Raymond
(74) *Attorney, Agent, or Firm*—Oyen Wiggs Green & Mutala LLP

(57) ABSTRACT

The invention provides a method for magnetic imaging of an object. The method comprises monitoring a magnetic field of sources in the object at a plurality of magnetic detectors to obtain a corresponding plurality of sensor outputs, monitoring a position of the object while monitoring the magnetic field of the sources, modeling the magnetic field of the sources in the object as a gradient of a scalar potential, the scalar potential comprising a sum of spherical harmonic functions each multiplied by a corresponding coefficient, and, compensating for the position of the object by applying a transformation to the plurality of sensor outputs, the transformation including, at least in part, a spherical harmonic translation transformation.

24 Claims, 2 Drawing Sheets

MOTION COMPENSATION IN BIOMAGNETIC MEASUREMENT

TECHNICAL FIELD

The invention relates to the measurement of biomagnetic signals. The invention has application to the magnetic imaging of biological structures. Some embodiments of the invention are used to compensate for head motion in magnetoencephalography.

BACKGROUND

Magnetoencephalography ("MEG") involves detecting magnetic fields produced within a subject's brain. Information about such biomagnetic fields is most useful when it can be associated with particular structures within the subject's brain to a spatial resolution of a few millimeters or better.

A typical MEG system comprises a helmet which carries a large number of magnetic detectors. The subject's head is placed inside the helmet. Magnetic signals originating from within the subject's head are detected at each of the magnetic detectors over a data acquisition period. The data acquisition period may, for example, be a few minutes.

Since biomagnetic signals are typically measured over significant time spans it is unreasonable to expect that a subject will be able to hold his or her head completely still throughout the measurement. Motions of the subject's head during the data acquisition period can interfere with the ability to associate particular magnetic signals with specific structures within the subject's brain. It is not practical to completely immobilize the subject's head.

One can localize the subject's head relative to the measured magnetic fields if the position of the subject's head relative to the magnetic detectors used to detect the magnetic fields is known. One way to localize a subject's head is to attach small coils at three or more known locations on the subject's head. The coils create fluctuating magnetic fields when alternating electrical currents are passed through them. Magnetic detectors are used to detect the coils' magnetic fields. The location of the coils, and thus the location of the subject's head, can be determined from the detected magnetic fields of the coils.

There is a need for biomagnetic measurement systems which can compensate for motion of the part of a subject being studied.

SUMMARY OF THE INVENTION

One aspect of this invention provides a method for magnetic imaging of an object. The method includes monitoring a magnetic field of sources in the object at a plurality of magnetic detectors to obtain a corresponding plurality of sensor outputs. A position of the object is monitored while monitoring the magnetic field of the sources. The magnetic field of the sources in the object is modeled as a gradient of a scalar potential. The scalar potential includes a sum of spherical harmonic functions each multiplied by a corresponding coefficient. The method includes compensating for changes in the position of the object by applying a transformation to the plurality of sensor outputs. The transformation includes, at least in part, a spherical harmonic translation transformation.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
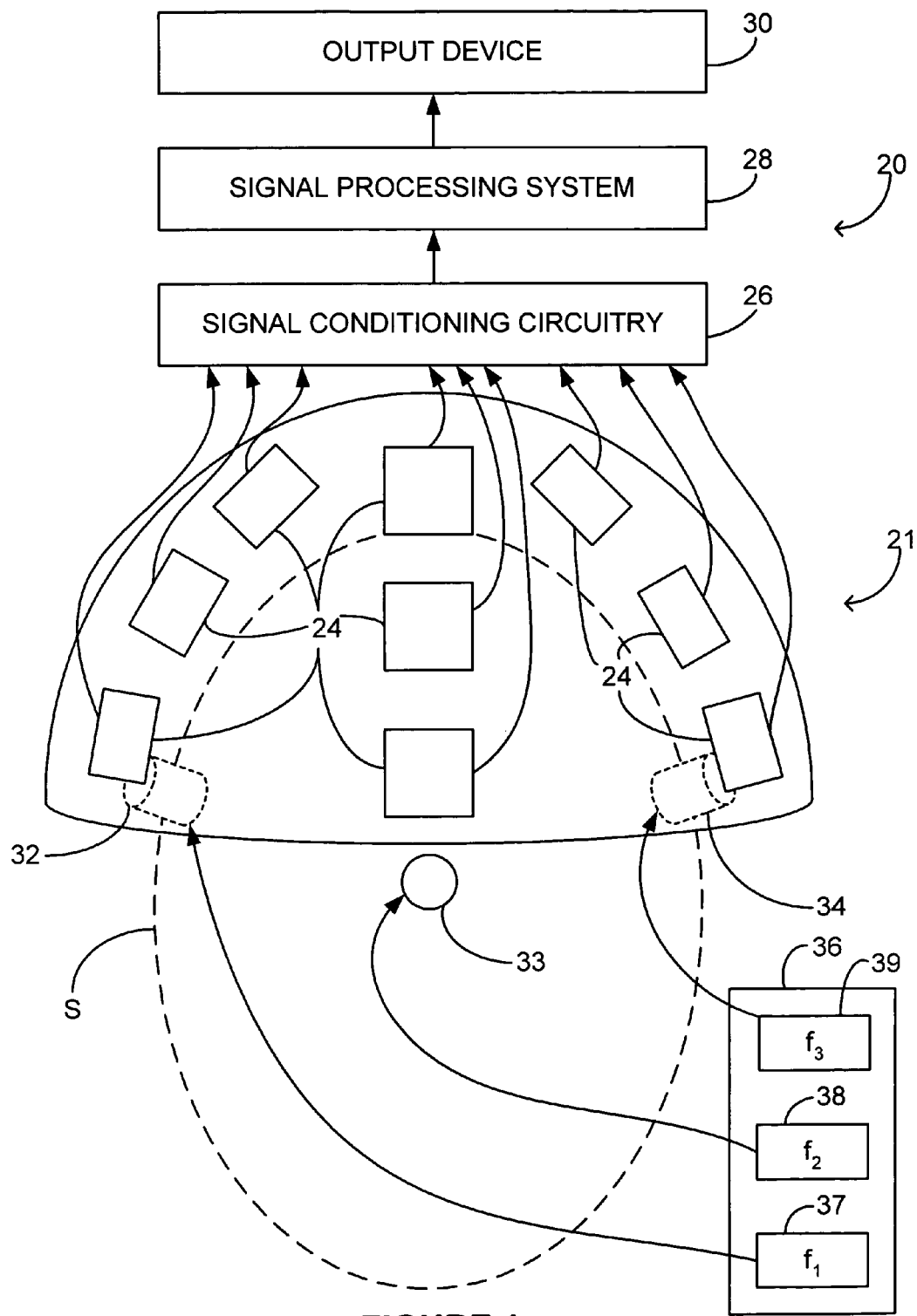
FIG. 1 is a schematic diagram of a MEG system which is used to measure biomagnetic fields according to one embodiment of the invention; and, FIG. 2 is a flow chart which illustrates a method for magnetic imaging of an object according to another embodiment of the invention.

FIG. 1 shows a MEG system 20 according to one embodiment of the invention. System 20 includes a number of magnetic detectors 24 which are located to detect magnetic fields originating within the head of a subject S. While FIG. 1 represents a detector array by only a few detectors 24, a MEG system typically has a few hundred detectors 24.

Detectors 24 may be SQUID detectors. Detectors 24 may comprise magnetic gradiometers and/or magnetometers. Signals from detectors 24 are appropriately conditioned by way of suitable signal conditioning circuitry 26. The processed signals are provided to a signal processing system 28. Signal processing system 28 generates output at an output device 30. The output may comprise, for example, a graphical display, a data file containing MEG data, or the like.

MEG system 20 includes a head localization system 21 capable of monitoring the position and orientation of the subject's head during the acquisition of MEG data. In the illustrated embodiment, head localization system 21 comprises a system as described in the co-pending and commonly owned patent application entitled METHOD AND APPARATUS FOR LOCALIZING BIOMAGNETIC SIGNALS being filed simultaneously herewith, which is hereby incorporated herein by reference. Any other suitable localization system, now known or developed in future which provides information about the position, or changes in position of a subject's head or other body part could be used as localization system 21.

In the illustrated embodiment, system 21 includes coils 32, 33 and 34. Coils 32, 33 and 34 are attached to the subject's head and are respectively driven with signals of frequencies $f_1, f_2$ and $f_3$ by a controller 36 which, in the illustrated embodiment includes oscillators 37, 38, and 39. Driving signals for coils 32, 33 and 34 may be obtained in any suitable manner.

System 21 monitors the locations of coils 32, 33 and 34. System 21 determines the position and orientation of the subject's head at various times based upon the locations of coils 32, 33 and 34. This may be done, for example, using methods described in the above-noted co-pending application.

During a data acquisition period, MEG system 20 monitors the outputs of magnetic detectors 24 and the position of the subject's head. This yields a sequence of samples of the outputs from each of magnetic detectors 24. System 20 generates a map of magnetic sources within the subject's head based upon the samples. System 20 compensates for motion of the subject's head based upon head position information provided by localization system 21.

Figure 2:
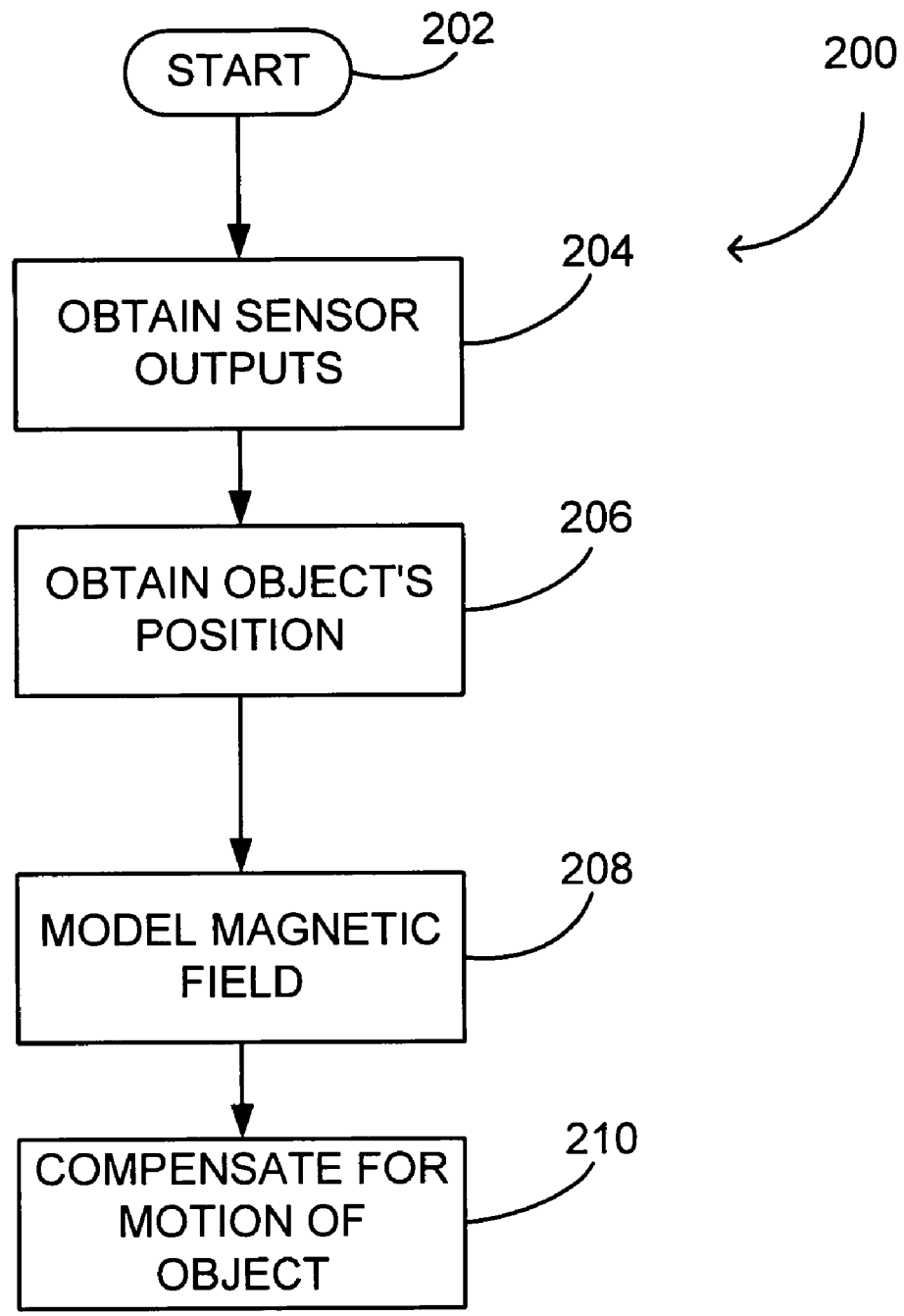

FIG. 2 is a flow chart illustrating a method 200 according to one embodiment of the invention. Method 200 may be used for magnetic imaging of an object having sources which produce magnetic fields, such as the head of subject S of FIG. 1. In a preferred embodiment, method 200 is carried out by MEG system 20 of FIG. 1. After method 200 begins at block 202, it obtains a plurality of outputs from detectors 24 at block 204. At block 206, method 200 obtains the object's position from localization system 21. At block 208, the magnetic field of the object is modelled as a gradient of a scalar potential comprising a sum of spherical harmonic functions each multiplied by a corresponding coefficient, as described further below. At block 210, method 200 compares the object's position obtained in block 206 with a reference position, and compensates for motion of the object by correcting the magnetic field modelled in block 208 to obtain a plurality of motion corrected sensor outputs. The compensation carried out in block 210 preferably comprises applying a transformation to the spherical harmonic functions, as described further below. The transformation includes a spherical harmonic translation transformation.

If one chooses a volume which includes detectors 24 but excludes any magnetic sources, the magnetic field detected by detectors 24 can be expressed as the gradient of a magnetic scalar potential Ψ. Within the volume, in which there are no magnetic sources, Ψ satisfies Laplace's equation:

$$\nabla^2 \Psi = 0 \tag{1}$$

Ψ can be expressed as a sum of spherical harmonic functions, for example, as follows:

$$\Psi(\vec{r}) = \sum_{l=1}^{\infty} \sum_{m=-l}^{l} \sum_{n=0}^{1} a_{lmn} Y_l^m(\theta, \phi) \left(\frac{r}{r_0}\right)^{n(2l+1)-(l+1)} \tag{2}$$

$$= \sum_{l=1}^{\infty} \sum_{m=-l}^{l} \sum_{n=0}^{1} a_{lmn} \psi_{lmn}(\vec{r})$$

where l, m and n are integer indices; $a_{lmm}$ are coefficients; $r_0$ is a normalizing radius; and $Y_l^m$ are given by:

$$Y_l^m = \begin{cases} \tilde{P}_l^m(\cos\theta)\cos(m\phi) & l \geq m \geq 0 \\ \tilde{P}_l^m(\cos\theta)\sin(m\phi) & -l \leq m < 0 \end{cases} \tag{3}$$

where $\tilde{P}_l^m$ is the Schmidt semi-normalized associated Legendre function given by:

$$\tilde{P}_l^m = (-1)^m \sqrt{(2-\delta_{m0})\frac{(l-|m|)!}{(l+|m|)!}} \; P_l^{|m|} \quad m \neq 0 \tag{4}$$

and $P_l^{|m|}$ is the standard associated Legendre function as defined, for example, in Abramowitz and Stegun, *Handbook of Mathematical Functions*, National Bureau of Standards, 1964. This formulation has the advantage that it does not require calculations involving complex number types and the normalization is the same for different terms. Spherical harmonic terms with n=0 are called internal terms, while terms with n=1 are called external terms. Sources inside the subject generate internal terms in the spherical harmonic expansion, while sources outside the volume containing the detectors generate external terms in the spherical harmonic expansion.

The spherical harmonic functions could be normalized in any suitable manner. The spherical harmonic functions may be expressed in other mathematically equivalent ways. For example, the spherical harmonic functions could be expressed in a format which uses complex variables as follows:

$$Y_l^m(\theta, \Phi) = P_l^m(\theta, \Phi)e^{im\phi} \tag{5}$$

Where there are M magnetic detectors 24, the signals from any one of the magnetic detectors may be represented as $B_i$ where i is an integer index corresponding to the magnetic detector with $1 \leq i \leq M$.

The method uses the values $B_i$ to determine values for a number N of the coefficients $a_{lmn}$ which yield a magnetic scalar potential which would produce the observed magnetic fields. N is larger than M and is chosen to be sufficiently large that the finite series:

$$\sum_{\mu=1}^{N} a_\mu f_\mu(\vec{r}) \tag{6}$$

is a good approximation to the true scalar potential of the magnetic field being modelled. In equation (6) $f_m(\vec{r})$ are spherical harmonic functions. N is not so large that the problem of determining values for the N coefficients becomes impractical.

The N coefficients $a_\mu$ are related to the M sensor outputs $B_i$ by an M×N matrix as follows:

$$B_n = \sum_{\mu=1}^{N} L_{n\mu} a_\mu \Leftrightarrow \vec{B} = \vec{L}\vec{a} \tag{7}$$

The matrix Ł (the "forward solution") is determined by the parameters of magnetic detectors 24 (e.g. their gain, coil position and size, and gradiometer order). The elements of Ł may be computed in advance based upon the known geometry and properties of magnetic detectors 24. A minimum norm algorithm may be used to identify a set of coefficients $a_\mu$ such that equation (7) is satisfied and a normalization function is minimized.

Various volume integrals of gradients of Ψ can be used as the normalization function for the scalar potential Ψ. The standard magnetic energy is one such volume integral. The magnetic energy can be expressed as:

$$E_1 = \int \sum_\mu \left(\frac{\partial \psi}{\partial r_\mu}\right)^2 dV \tag{8}$$

An alternate normalizing function is given by:

$$E_2 = \int \sum_{\mu\nu} \left(\frac{\partial^2 \psi}{\partial r_\mu \partial r_\nu}\right)^2 dV \tag{9}$$

$E_2$ is a better choice for use as the normalization function where first-order gradiometers are used to detect the magnetic field. If magnetic detectors 24 include a sufficient number of higher-order gradiometers, then total second or higher-order derivatives could be used as the normalizing functions. A linear combination of $E_1$, $E_2$ and/or other total higher-order derivatives could also be used as the normalization function. In an example embodiment, magnetic detectors 24 comprise first order gradiometers and the normalization function $E_2$ defined by equation (9) is used as the normalization function.

When $\Psi$ is represented by a spherical harmonic expansion the Equation (8) may be expressed as a matrix equation involving the N×N energy matrix $\vec{K}$ as follows:

$$E_2 = \sum_{p,q} a_p K_{pq} a_q \tag{10}$$

where p and q each represent a particular set of values {l, m, n } and the summation in Equation (10) is performed over those N sets of values corresponding to the N spherical harmonic functions to be included in the model. Where the volume of integration is a spherical shell having inner radius $r_1$, and outer radius $r_2$, the elements of $\vec{K}$ are given by two internal basis functions and two external basis functions. The two internal basis functions are given by:

$$K_{ml0,\mu\lambda 0} = 4\pi(l+1)(l+2)\left[\left(\frac{r_0}{r_1}\right)^{2l+3} - \left(\frac{r_0}{r_2}\right)^{2l+3}\right]\delta_{m\mu}\delta_{l\lambda} \tag{11}$$

The two external basis functions are given by:

$$K_{ml1,\mu\lambda 1} = 4\pi l(l-1)\left[\left(\frac{r_2}{r_0}\right)^{2l-1} - \left(\frac{r_1}{r_0}\right)^{2l-1}\right]\delta_{m\mu}\delta_{l\lambda} \tag{12}$$

where $r_0$ is a normalizing radius. The internal functions (n=0) and external functions (n=1) are orthogonal and so $K_{ml0,ml1}=0$. It is desirable to select a spherical integration volume because the energy matrix may be nearly singular, in at least some cases, if the integration volume does not extend over all angles (e.g. where integration is performed over a range of angle θ which is smaller than $0 \leq \theta < \pi$).

The formal solution for the set of coefficients $\vec{a}$ that yields the observed values for $\vec{B}$ and also minimizes the energy function $E_2$ is:

$$\vec{a} = K^{-1}L^T(LK^{-1}L^T)^{-1}\vec{B} = \vec{\vec{Q}}\vec{B} \tag{13}$$

where $\vec{\vec{Q}}$ is the backward solution matrix. $\vec{\vec{Q}}$ depends only upon the locations and properties of magnetic detectors 24. The matrix $LK^{-1}L^T$ typically has a number of small eigenvalues. It is therefore generally necessary to regularize this matrix to obtain an approximation for $\vec{\vec{Q}}$. The matrix can be regularized by any suitable mathematical technique, such as single value decomposition. One approach to performing single value decomposition is described by Uutela, K. et al. *Visualization of magnetoencephalographic data using minimum current estimates*, Neurolmage v. 10, (1999) pp. 173–180. Tikhonov regularization is another type of procedure that may be performed to regularize $LK^{-1}L^T$.

In some alternative embodiments of the invention, N is smaller than or equal to M (the number of sensors). In these embodiments the scalar potential is again approximated by the finite series of equation (6). The relationships between the coefficients and the measurements is given by:

$$B_n^{fit} = \sum_{\mu=1}^{N} L_{n\mu} a_\mu \tag{14}$$

These embodiments use a fitting process to identify a set of coefficients which provides an estimate of the scalar potential representing a best fit to the measured data. For example, the fitting process may identify a solution (i.e. a set of coefficients a) that minimizes a weighted sum of errors in the fit to data B as follows:

$$F_2 = \sum_{m,n=1}^{M} (B_m^{fit} - B_m)W_{mn}(B_n^{fit} - B_n) \tag{15}$$

where W is a positive definite matrix. W may be chosen to be the M×M identity matrix. If so, the solution which minimizes $F_2$ is:

$$\vec{a} = (L^TWL)^{-1}W\vec{B} = \vec{\vec{Q}}\vec{B} \tag{16}$$

where $\vec{\vec{Q}}$ is the backward matrix for the case $N \leq M$.

A spherical harmonic representation of the magnetic scalar potential can be used to compensate for motion of the subject's head. In general, any head motion can be broken down into a 3-dimensional rotation and a 3-dimensional translation. Knowing the rotational and translational properties of the spherical harmonic components of the potential, one can derive a mathematical relationship which transforms the actual outputs of magnetic detectors 24 to the outputs that would have been measured had the subject's head remained stationary.

Spherical harmonic functions have a simple behaviour under rotations. For a single value of the spherical harmonic degree l, the coefficients $a_{lmn}$ are transformed by a rotation according to:

$$\tilde{a}_{lmn} = \sum_{\mu=-l}^{l} R_{m\mu}^{(l)} a_{l\mu n} \tag{17}$$

where $\tilde{a}_{lmn}$ are the transformed coefficients and $R_{m\mu}^{(l)}$ are the elements of a rotation matrix. Rotation does not mix spherical harmonics with different values of l. $\vec{R}^{(l)}$ is a unitary order –(2l+1) matrix. Expressions for the rotation matrix are provided in D. A. Varshalovich. et. al., *Quantum Theory of Angular Momentum*, World Scientific, Singapore (1988) ISBN 9971-50-107-4.

There is no simple matrix for performing spatial translations of the spherical harmonic functions. Spherical harmonic functions have no special symmetry under translations. It can be shown that the shifted and unshifted inner harmonic coefficients are related by the matrix equation:

$$\tilde{a}_{\lambda\mu0}(\vec{u}) = \sum_{lm} T_{\lambda\mu,lm} a_{lm0} \quad (18)$$

where the elements of $\vec{T}$ are given by:

$$T(\vec{u})_{\lambda\mu,lm} = \frac{2\lambda+1}{4\pi} \int_{\theta=0}^{\pi} \int_{\phi=0}^{2\pi} Y_{\lambda\mu}\left(\frac{\vec{r}}{|\vec{r}|}\right) \left[\frac{|\vec{r}|}{\vec{r}_o}\right]^{-(\lambda+1)} \quad (19)$$

$$Y_{lm}\left(\frac{\vec{r}-\vec{u}}{|\vec{r}-\vec{u}|}\right) \left[\frac{|\vec{r}-\vec{u}|}{\vec{r}_o}\right]^{-(\lambda+1)} \sin\theta d\theta d\phi$$

The elements of $\vec{T}$ can be determined numerically or by published methods. For example, M Danos et. al. *Multiple Matrix Elements of the Translation Operator* J. MathPhys. V.6, pp 766–778 (1965) describes spherical harmonic translation transformations. Certain elements of $\vec{T}$ are zero. Each element of the matrix $\vec{T}$ is a simple polynomial function of the components of the vector $\vec{u}$. The polynomial coefficients may be precalculated and stored to facilitate fast computation of $\vec{T}(\vec{u})$.

To derive a matrix that transforms the outputs from magnetic detectors 24 to the values that those outputs would have had if the subject's head had not been moved, one can combine a rotation matrix, $\vec{R}$, a spherical harmonic function shift matrix, $\vec{T}$, a regularized backwards matrix $\vec{Q}$ and the forward matrix $\vec{L}$ as follows:

$$\vec{B}(0,0)_m \approx \vec{L}(0,0)_{mp} [\vec{R}^{(a)}]_{pq}^{-1} \vec{T}(-\vec{u})_{qs} \vec{Q}(0,0)_{sv} \vec{B}(R,\vec{u})_v \quad (20)$$

where $\vec{B}(0,0)$ is a vector of the corrected magnetic detector outputs; $\vec{B}(R,\vec{u})_v$ is a vector of the actual magnetic detector outputs for the subject's head at an actual position and orientation which differ from the reference position and orientation (0,0) by the rotation R and the translation $\vec{u}$. In general, equation (20) is an approximation because $\vec{Q}$ is regularized in the case where N>M or coefficients for the spherical harmonic functions are a best fit to measured data in the case where N<M.

One can vary the number of terms in the spherical harmonic expansion used as an estimate of the scalar magnetic potential. For MEG in which a goal is to model electric current dipole sources at a distance of approximately 9 cm from magnetic detectors 24, it is desirable to use internal spherical harmonics having values of l up to at least l=12, preferably l=14 and most preferably at least l=18 and at least external spherical harmonics having l=2, 3 and 4. Choosing internal spherical harmonic functions with l={1, 2, . . . ,18} and external spherical harmonic functions with l={2,3,4} results in N=381 spherical harmonic functions. Choosing internal spherical harmonic functions with l={1, 2, . . . ,14} and external spherical harmonic functions with l={2,3,4} results in N=309 spherical harmonic functions.

In general it is desirable that there be more spherical harmonic functions in the expansion of the scalar potential than there are magnetic detectors 24 used in determining the coefficients corresponding to the spherical harmonic functions. This permits a solution to be obtained by minimizing a total gradient as illustrated, for example, in equation (7). As noted above, some embodiments of the invention use fewer spherical harmonic functions than sensors. These embodiments can use a fitting process as illustrated, for example, by equation (15).

The approximation of the scalar potential may include one or more terms in addition to spherical harmonic terms. In some embodiments the scalar potential is expressed as:

$$\sum_{\mu=1}^{N} a_\mu f_\mu(\vec{r}) + a' g(\vec{r}) \quad (21)$$

where a' is a coefficient and $g(\vec{r})$ is a function. $g(\vec{r})$ may model the contribution to the scalar potential from one or more known external magnetic sources. For example, the magnetic field produced by a subject's heart may be modelled as a point-like magnetic source. The potential from a point source of strength $\vec{M}$ is given by:

$$g(\vec{r}) = \frac{\vec{m} \cdot (\vec{r}-\vec{s})}{|\vec{r}-\vec{s}|^3} \quad (22)$$

A long series of external spherical harmonic functions could be needed to approximate the contribution of such a source to the scalar magnetic potential to the same accuracy as equation (21).

The processes described above for determining the coefficients a can also be used where the scalar potential includes one or more additional terms as described above. The translation and rotation operations would need to be modified to perform translation and rotation in a manner appropriate to the function $g(\vec{r})$. Where $g(\vec{r})$ is a simple function as in equation (21) performing translation and/or rotations can be performed by way of straightforward translation and rotation operators.

Certain implementations of the invention comprise computer processors which execute software instructions which cause the processors to perform a method of the invention. For example, one or more processors in a controller for a MEG system may implement a method as shown in FIG. 2 by executing software instructions from a program memory accessible to the processor(s). The invention may also be provided in the form of a program product. The program product may comprise any medium which carries a set of computer-readable signals comprising instructions which, when executed by a computer processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like or transmission-type media such as digital or analog communication links.

In some embodiments of the invention, signal processing system 28 permits a user to specify how many spherical harmonic functions will be used in estimating the scalar potential. For example, a user interface to signal processing system 28 may permit a user to specify a maximum value of l for internal spherical harmonic terms to be used in the approximation for the scalar potential and a range of values of l to be used for external spherical harmonic terms. For example, the user may choose to use external spherical harmonic terms for values of l=2 to l=3 or l=2 to l=4 or the user may choose not to include any external spherical harmonic terms at all. The signal processing system may automatically determine N based upon the user input and may then select an appropriate process for determining the coefficients depending upon whether M<N or N<M.

Where a component (e.g. a software module, processor, detector, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

Magnetic detectors 24 may be of any suitable types. For example, detectors 24 could include magnetometers and/or first or second order magnetic gradiometers.

While the invention is discussed above in the context of a MEG system, the invention may be applied to magnetic imaging of other biological systems or other objects which move relative to an array of magnetic sensors.

Accordingly, the scope of the invention is to be construed in accordance with the substance defined by the following claims.

What is claimed is:

1. A method for magnetic imaging of an object, the method comprising:
   monitoring a magnetic field of sources in the object at a plurality of magnetic detectors to obtain a corresponding plurality of sensor outputs;
   while monitoring the magnetic field of the sources, monitoring a position of the object;
   modeling the magnetic field of the sources in the object as a gradient of a scalar potential, the scalar potential comprising a sum of spherical harmonic functions each multiplied by a corresponding coefficient; and,
   compensating for changes in the position of the object by applying a transformation to the plurality of sensor outputs, the transformation including, at least in part, a spherical harmonic translation transformation.

2. A method according to claim 1 wherein the scalar potential comprises at least one additional term in addition to the spherical harmonic functions.

3. A method according to claim 2 wherein the additional term comprises a potential corresponding to point dipole sources.

4. A method according to claim 3 wherein the additional term comprises a potential corresponding to point current dipole source.

5. A method according to claim 3 wherein the additional term has a distance dependance such that the term drops off with distance at least as quickly as the inverse square of the distance.

6. A method according to claim 3 wherein the additional term is of the form: $a'g(\vec{r})$ where a' is a coefficient and $g(\vec{r})$ is a function of a position $\vec{r}$.

7. A method according to claim 6 wherein $g(\vec{r})$ is given by:

$$\frac{\vec{m} \cdot (\vec{r} - \vec{s})}{|\vec{r} - \vec{s}|^3}$$

where $\vec{s}$ is a fixed position; and $\vec{m}$ is a dipole moment.

8. A method according to claim 1 wherein a number N of the spherical harmonic functions exceeds a number M of the plurality of magnetic detectors.

9. A method according to claim 8 wherein the corresponding coefficients for the spherical harmonic functions are obtained by applying a M×N forward solution matrix to the plurality of sensor outputs.

10. A method according to claim 9 wherein elements of the forward solution matrix are computed based upon geometry and properties of the plurality of detectors.

11. A method according to claim 1 wherein a number N of the spherical harmonic functions is less than a number M of the plurality of magnetic detectors.

12. A method according to claim 11 wherein modeling the magnetic field of the sources comprises performing a fitting process.

13. A method according to claim 12 wherein the fitting process comprises performing a least squares computation.

14. A method according to claim 1 wherein compensating for the position of the object comprises applying a forward solution matrix to the plurality of sensor outputs.

15. A method according to claim 1 wherein compensating for the position of the object comprises applying a regularized backward solution matrix to the plurality of sensor outputs.

16. A method according to claim 15 comprising regularizing the backward solution matrix by performing a Tikhonov regularization.

17. A method according to claim 1 wherein compensating for the position of the object comprises applying a rotation matrix to the plurality of sensor outputs.

18. A method according to claim 1 wherein compensating for the position of the object comprises calculating a vector of corrected sensor outputs $\vec{B}(0,0)$ according to the formula:

$$\vec{B}(0,0)_m \approx \vec{\vec{K}}(0,0)_{mp}[\vec{\vec{R}}^{(a)}]_{pq}^{-1}\vec{\vec{T}}(-\vec{u})_{qs}\vec{\vec{Q}}(0,0)_{sv}\vec{B}(R,\vec{u})_v,$$

or a mathematical equivalent thereof, where $\vec{B}(R,U)$ is a vector of the plurality of sensor outputs for the position of the object which differs from a reference position (0,0) by the rotation R and the translation U, $\vec{\vec{Q}}(0,0)$ is a regularized backward solution matrix, $\vec{\vec{T}}(-\vec{u})$ is a spherical harmonic function translation matrix, $\vec{\vec{R}}^{(a)}$ is a spherical harmonic function rotation matrix, and $\vec{\vec{K}}(0,0)$ is a forward solution matrix.

19. A method according to claim 1 wherein the corresponding coefficients for the spherical harmonic functions are selected such that a normalization function is minimized.

20. A method according to claim 19 wherein the energy function comprises an integral of a derivative of the scalar potential over a volume wherein the volume includes the sensors.

21. A method according to claim 20 wherein the volume comprises a spherical shell.

22. A method according to claim 20 wherein magnetic detectors comprise a plurality of magnetometers and the normalization function comprises:

$$E_1 = \int \sum_\mu \left(\frac{\partial \Psi}{\partial r_\mu}\right)^2 dV.$$

23. A method according to claim 20 wherein the energy function comprises a linear combination of:

$$E_1 = \int \sum_\mu \left(\frac{\partial \Psi}{\partial r_\mu}\right)^2 dV \text{ and}$$

$$E_2 = \int \sum_{\mu\nu} \left(\frac{\partial^2 \Psi}{\partial r_\mu \partial r_\nu}\right)^2 dV.$$

24. A method according to claim 19 wherein the plurality of magnetic detectors comprise a plurality of first order gradiometers and wherein the energy function comprises:

$$E_2 = \int \sum_{\mu\nu} \left|\frac{\partial^2 \Psi}{\partial r_\mu \partial r_\nu}\right|^2 dV,$$

where $\Psi$ is the scalar potential.

* * * * *